US00PP10615P

United States Patent [19]

Osiecki

[11] Patent Number: Plant 10,615

[45] Date of Patent: Sep. 22, 1998

[54] SPATHIPHYLLUM PLANT 'S24'

[75] Inventor: Marian W. Osiecki, Marianna, Fla.

[73] Assignee: Oglesby Plant Laboratories, Inc., Altha, Fla.

[21] Appl. No.: 804,985

[22] Filed: Feb. 25, 1997

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Rothwell, Figg, Ernst & Kurz, pc

[57] ABSTRACT

A new and distinct cultivar of Spathiphyllum is provided. The plant is large, full, symmetrical, suitable for production in a 15–25 cm pot from a single tissue culture produced microcutting; maintains proper growth habit and leaf shape at crowded pot spacing; grows vigorously; branches freely; flowers naturally producing good quality inflorescences from the onset of flowering; has large, wide, thick, dark green, glossy leaves; thick, strong, straight peduncles and large, bright white spathes with very little green coloration, held relatively close to foliage.

2 Drawing Sheets

This invention relates to a new and distinct Spathiphyllum cultivar characterized by the following combination of repeatedly observed traits:

1. Large size,
2. full and symmetrical growth habit,
3. growth habit and leaf shape maintained at crowded pot spacing,
4. vigorous growth,
5. abundant branching,
6. good quality inflorescences from the onset of flowering,
7. large, wide, dark green, glossy leaf blades,
8. thick, strong, straight peduncles,
9. large, bright white spathes with very little green coloration, held relatively close to foliage;

and primarily selected for those characteristics being so selected from the progeny of the cross stated below in a cultivated area near Altha, Fla.

ORIGIN AND ASEXUAL REPRODUCTION

The new cultivar is a product of a planned breeding program carried out at Oglesby Plant Laboratories, Inc. near Altha, Fla. The female parent was a selected clone of Spathiphyllum 'Viscount' and the male parent was a selected clone of Spathiphyllum 'Supreme'. The cross was made in 1991, the plant was selected in 1993 and has since been reproduced by tissue culture in the vicinity of Altha, Fla. with the characteristics stated, found to be maintained through successive generations.

This new cultivar has been identified as Spathiphyllum 'S24'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S24' was approximately 20 months from planting a single tissue culture produced microcutting and was grown in a 25 cm pot.

In the photographs:

DETAILED DESCRIPTION OF THE NEW CULTIVAR

Figure 1:
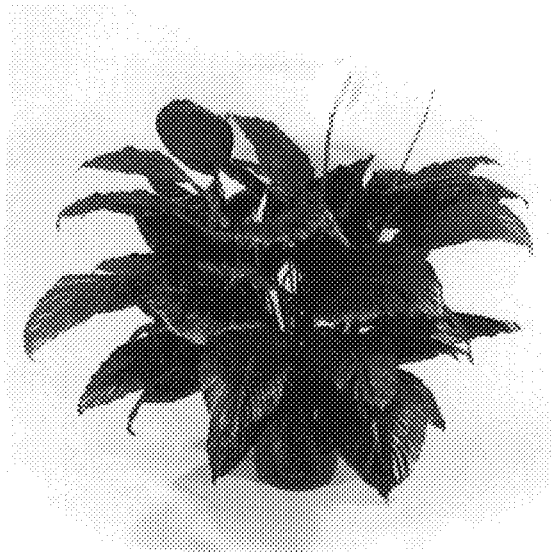
FIG. 1 depicts the whole plant.
Figure 2:
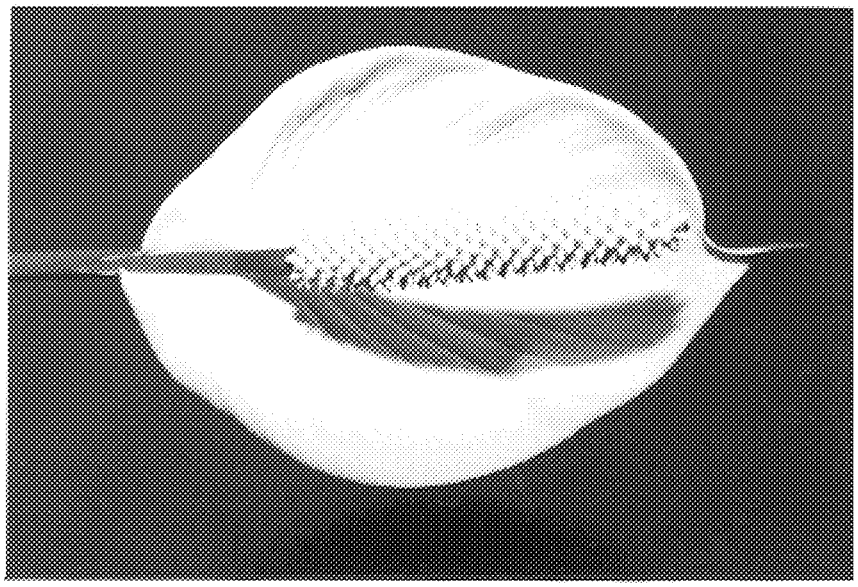
FIG. 2 illustrates the mature inflorescence.
Figure 3:
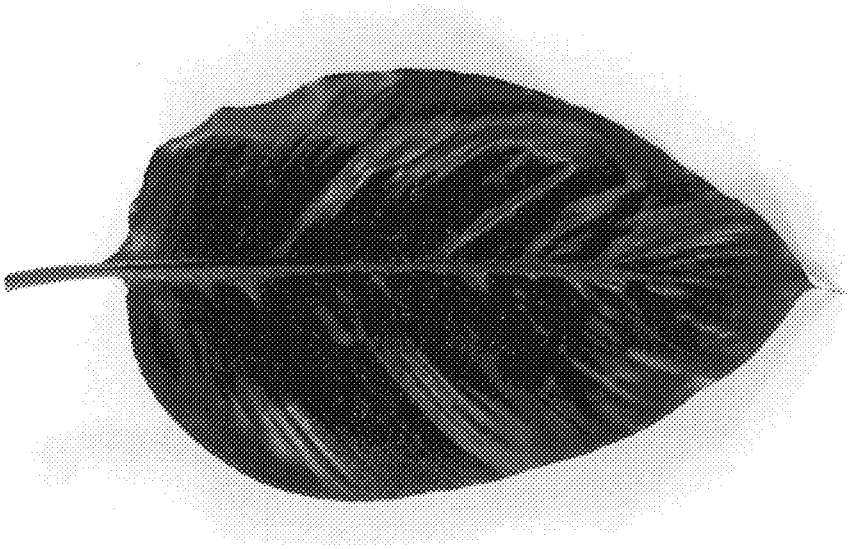
FIG. 3 illustrates the top of a mature leaf.
Figure 4:
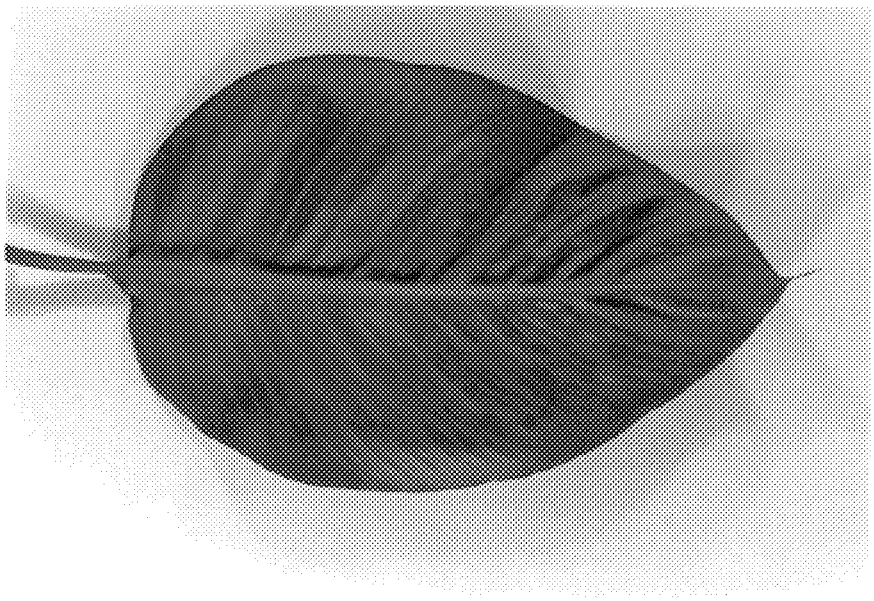
FIG. 4 illustrates the bottom of a mature leaf.

The following observations and measurements describe plants grown near Altha, Fla. under greenhouse conditions. These observations and measurements were recorded in February, 1997 from mature plants (about 20 months from planting tissue culture produced microcuttings) grown in 25 cm pots. Fully developed organs on main stems were used for measurements. Color values were determined on Feb. 3, 1997, under natural. indirect light of approximately 400–650 foot-candles. Color references are made to The R.H.S. Colour Chart, except where general color terms of ordinary significance are used.

'S24' has not been observed under all possible environmental conditions. The phenotype may vary with variations in environment and horticultural practices, such as temperature, light intensity, day length, fertilization, propagation method, etc., without any change in genotype.

Parentage:

*Female parent.*—Selected clone of Spathiphyllum 'Viscount'.

*Male parent.*—Selected clone of Spathiphyllum 'Supreme'.

Propagation: Plant tissue culture.

Plant:

*Growth habit.*—Large, full, symmetrical, well branched (up to 8 side shoots), with distinct main stem.

*Height.*—Foliage 59–71 cm, with spathes 75–96 cm.

*Maximum width.*—101–117 cm.

Petiole:

*Length.*—Leaf supporting inflorescence 31.5–40.5 cm; leaf penultimate to leaf supporting inflorescence 27.0–33.0 cm.

*Diameter* (*Immediately below geniculum*).—Leaf supporting inflorescence: 5.7–6.9 mm; leaf penultimate to leaf supporting inflorescence: 6.1–7.4 mm.

*Geniculum.*—Leaf supporting inflorescence: 3.3–4.6 cm long, 6.6–8.0 mm in diameter; leaf penultimate to leaf supporting inflorescence: 3.9–5.5 cm long, 7.4–8.3 mm in diameter.

Leaf blade:

*Shape.*—Elliptic to ovate, width divided slightly unequally by midrib; tip acuminate with some cuspidate tendencies, slightly curved, base obtuse with some cuneate tendencies, narrowly decurrent on peduncle; margin slightly wavy.

*Size.*—Leaf supporting inflorescence: 31.0–38.0 cm long by 17.0–20.5 cm wide; length:width ratio 1.6–2.0:1. Leaf penultimate to leaf supporting inflorescence: 33.5–37.5 cm long by 17.6–20.6 cm wide; length:width ration 1.7–1.9:1. Leaf blades on young side shoots and leaf blades produced on main stem immediately after inflorescence are smaller, substantially narrower and have more cuneate bases.

*Texture.*—Smooth, glossy; young leaves highly polished.

*Veins.*—Well defined and sunken in the adaxial leaf surface.

*Color.*—Mature leaf: Adaxial: much darker than 147A (yellow-green). Abaxial: 147B Young newly unrolled leaf: Adaxial: more yellow than 137 B-C (green); more green than 146A or 147B (both yellow-green). Abaxial: similar to 147B.

Inflorescence:

*Arrangement.*—Spathes carried on thick, strong, usually straight peduncles relatively close to foliage; peduncle occasionally slightly bends in its distal portion. Spadix long in relation to spathe (spathe length:spadix length ratio 1.6–1.9:1). Inflorescences on young side shoots smaller than on the main stem.

Peduncle:

*Size.*—70.0–79.0 cm long; 6.8–7.2 mm in diameter immediately below spathe.

*Color.*—Front: 146 B-C (yellow-green) immediately below spathe, proximally becomes slightly darker (146 A-B). Back: 146 B.

*Stipe.*—1.0–1.6 cm long, 5.3–6.3 mm in diameter.

Spathe:

*Shape.*—Elliptic, cupped through senescence; tip-acuminate with cusipdate tendencies, twisted; base cuneate, variably asymmetric.

*Size.*—15.5–20.7 cm long by 9.3–10.7 cm wide; length: width ratio 1.6–1.9:1.

*Color.*—155 D (white). Green occurs only on midrib and tip. On back side at base of stipe midrib is similar to, but more green than 146A (yellow-green) and more yellow than 137A (green). Distally coloration on the midrib becomes lighter, more yellow, and in the distal half is a very fine line 146C or 144B-C (both yellow-green), except for the most distal approximately 3–4 cm, where it slightly widens and becomes darker (146A, 144A). In this most distal zone there is some diffused yellow-green (144B-C, 146D) on both sides of the midrib. On some inflorescences the green line is absent from the proximal portion of the distal half. On the front side the green coloration is confined to a very fine line in the distal 3–4 cm of the midrib and some additional diffused green in the tip.

Spadix:

*Size.*—9.0–11.0 cm long; 1.8–2.0 cm in diameter.

*Color.*—158 A (yellow-white).

Botanical flower:

*Perianth.*—Visible between pistils, segments united.

*Pistil.*—Acute.

*Stamens.*—Not visible before pollen release.

Flowering: Flowers naturally in 15 cm pots, approximately 8–10 months from planting tissue culture produced microcuttings, producing good quality inflorescences from the onset of flowering. In a 25 cm pot at approximately 20 months one to four white spathes present above foliage.

Roots: Numerous, cream-brown main roots with cream-yellow root cap, numerous cream lateral roots.

Disease and insect resistance: No unusual susceptibility to diseases or insects noted to date.

Comparison with the Known Cultivars

The new cultivar can be compared to the known cultivars 'Supreme' and 'Viscount'. Observations for comparisions were made on plants grown under similar conditions in a greenhouse near Altha, Fla.

'S24' is distincuished from 'Supreme' by its more compact, less upright, more symmetrical growth habit, especially at crowded pot spacing; earlier and more abundant branching; better quality inflorescences at the onset of flowering; shorter petioles; shorter, more roundish, thicker, much darker and glossier leaf blades; shorter peduncles; narrower spathes of a brighter white color held closer to foliage.

'S24' is further distinguished from 'Viscount' by its taller and more upright growth habit; larger, more roundish and slightly darker leaf blades; thicker, stronger peduncles and larger spathes held closer to foliage.

I claim:

1. A new and distinct cultivar of Spathiphyllum plant named 'S24', substantially as described and illustrated herein, characterized particularly as to novelty by its large size; vigorous growth; abundant branching; large, wide, dark, glossy leaf blades; large spathes of bright white color with limited green coloration, held on thick, strong peduncles relatively close to foliage.

* * * * *